United States Patent [19]
Hofmann

[11] Patent Number: 5,273,525
[45] Date of Patent: Dec. 28, 1993

[54] INJECTION AND ELECTROPORATION APPARATUS FOR DRUG AND GENE DELIVERY

[75] Inventor: Gunter A. Hofmann, San Diego, Calif.

[73] Assignee: BTX Inc., San Diego, Calif.

[21] Appl. No.: 929,103

[22] Filed: Aug. 13, 1992

[51] Int. Cl.⁵ .............................................. A61N 1/04
[52] U.S. Cl. .............................. 604/21; 604/51; 607/116
[58] Field of Search ........... 604/21, 49, 51, 274; 128/421, 419 R, 784, 786, 642

[56] References Cited

U.S. PATENT DOCUMENTS

| | | | |
|---|---|---|---|
| 449,651 | 3/1891 | Bartsch | 604/21 |
| 4,411,657 | 10/1983 | Galindo | 604/274 |
| 4,776,349 | 10/1988 | Nashef | 604/21 |
| 5,081,990 | 1/1992 | Deletis | 128/642 |
| 5,119,832 | 6/1992 | Xavier | 604/51 |

*Primary Examiner*—William E. Kamm
*Assistant Examiner*—George Manuel
*Attorney, Agent, or Firm*—Baker, Maxham, Jester & Meador

[57] ABSTRACT

An apparatus for implanting macromolecules such as genes, DNA or pharmaceuticals into a preselected tissue region such as a muscle or an organ of a patient. A modified syringe is provided for injecting a predetermined quantity of a fluid medium carrying the preselected macromolecules. A signal generator is connected to the syringe for generating a predetermined electric signal. The syringe includes a pair of electrodes which are connected to the signal generator for applying an electric field in the tissue region. The field has a predetermined strength and duration in order to make the walls of a plurality of cells in the tissue region transiently permeable to permit the macromolecules to enter said preselected cells without damaging said cells. This enhances the uptake of macromolecules and thus enhances the therapeutic effect achieved. Alternate embodiments having twin needles and a blade may be utilized.

20 Claims, 1 Drawing Sheet

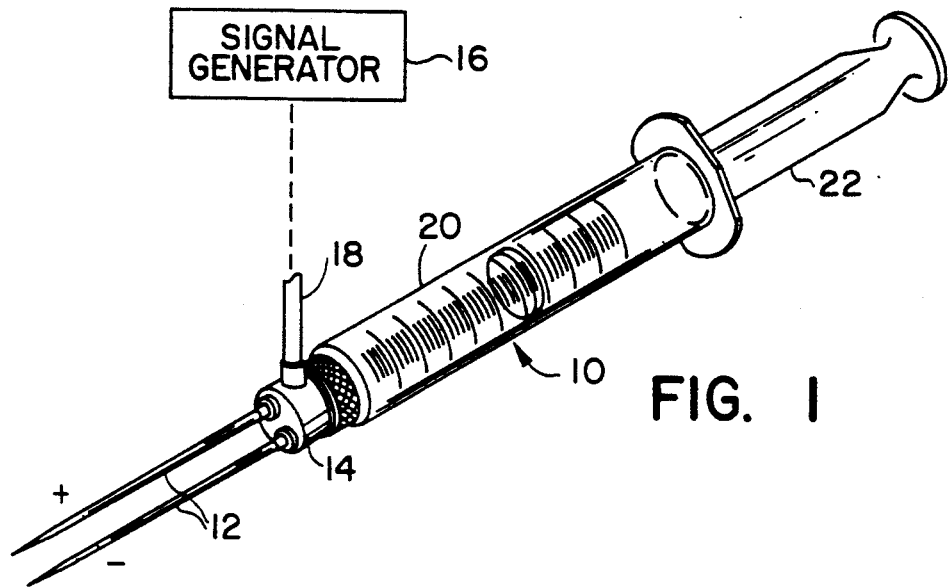
FIG. 1
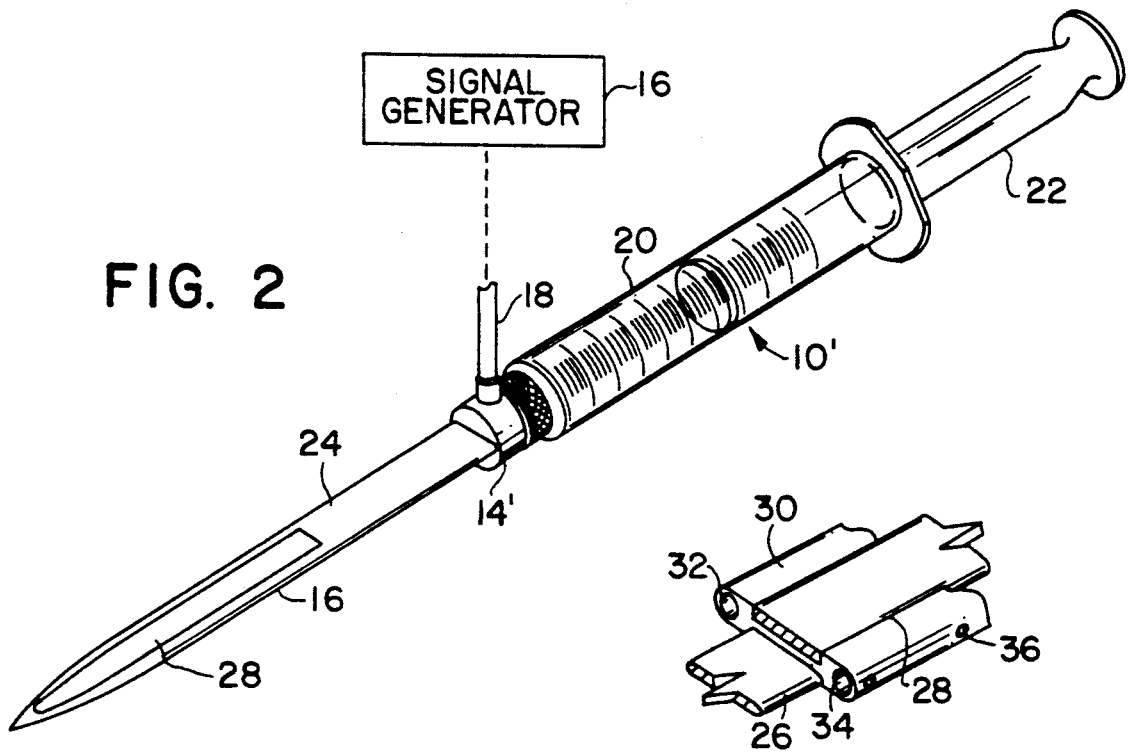
FIG. 2
FIG. 3

INJECTION AND ELECTROPORATION APPARATUS FOR DRUG AND GENE DELIVERY

BACKGROUND OF THE INVENTION

The present invention relates to the treatment of ailments in humans and other mammals, and more particularly, to apparatus for delivering pharmaceutical compounds and genes into live cells of a patient.

It is known that DNA can be directly injected into the muscle of a mouse to cause production of the protein it encodes. This technique may allow physicians to treat human diseases with therapeutic genes. The injected genes may cause the muscle tissue to produce the desired proteins for as long as several months. Similar expression has been shown in lung, brain and skin tissues. See Genetic Technology News: Volume 10, Number 4, Apr. 1990. A shortcoming of the known injection technique is the relatively low yield of gene uptake.

SUMMARY OF THE INVENTION

Accordingly, it is the primary object of the present invention to provide an apparatus that will improve the uptake of genes and other macromolecules in muscles, organs and other tissues.

It is another principal object of the present invention to provide a method of enhancing the uptake of genes and other macromolecules in muscles, organs and other tissues.

The present invention provides an apparatus for implanting macromolecules such as genes, DNA or pharmaceuticals into a preselected tissue region of the patient such as a muscle or an organ of a patient. A modified syringe is provided for injecting a predetermined quantity of a fluid medium carrying the preselected macromolecules. A signal generator is connected to the syringe for generating a predetermined electric signal. The syringe includes a pair of electrodes which are connected to the signal generator for applying an electric field in the tissue region. The field has a predetermined strength and duration in order to make the walls of a plurality of cells in the tissue region transiently permeable to permit the macromolecules to enter said preselected cells without damaging said cells. This enhances the uptake of macromolecules and thus enhances the therapeutic effect achieved. Alternate embodiments having twin needles and a blade may be utilized.

BRIEF DESCRIPTION OF THE DRAWINGS

FIG. 1 illustrates a first embodiment of the injection and electroporation apparatus of the present invention.

FIG. 2 illustrates a second embodiment of the injection and electroporation apparatus of the present invention.

FIG. 3 is an enlarged fragmentary view illustrating construction details of the second embodiment.

Throughout the drawing figures, like reference numerals refer to like parts.

DESCRIPTION OF THE PREFERRED EMBODIMENTS

The present invention takes advantage of the phenomenon known as electroporation in order to improve the uptake of genes, DNA and/or pharmaceuticals, hereinafter "macrolecules", into muscles, organs and other tissues of humans and other living organisms. Electroporation involves the transient formation of pores in cell membranes utilizing short pulses of high intensity electric fields. DNA and other macromolecules can enter the cells after pores are formed in the cell walls. Thereafter they stay encapsulated in the cells and the cell walls reseal themselves. The DNA can combine with the genome of the cells and alter their genetic properties.

Referring to FIG. 1, a first embodiment of the apparatus of the present invention comprises a hypodermic syringe 10 having a pair of closely spaced, parallel hollow needles 12 which serve as electrodes. The needles are physically supported by a hub 14 and are electrically connected to a signal generator 16 via cable 18. A fluid medium carrying the macromolecules is contained within the barrel 20 of the syringe 10. Once the needles 12 are implanted in a preselected tissue region of a patient, a plunger 22 of the syringe is depressed to inject the fluid into the region. While the needles are still implanted, the signal generator 16 is energized. The function of the signal generator 16 is to generate a predetermined electric signal which, when applied to the needle electrodes 12 of the syringe, results in applying electric fields of a predetermined strength and duration to the preselected tissue region. Preferably these fields are applied repeatedly and their strength and duration make the walls of preselected cells sufficiently permeable to permit the macromolecules to enter the cells in the preselected tissue region in the without damaging them.

One suitable signal generator is the ELECTRO CELL MANIPULATOR Model ECM 600R commercially available from BTX, Inc. of San Diego, Calif., U.S.A. The ECM 600 signal generator generates a pulse from the complete discharge of a capacitor which results in an exponentially decaying waveform. The electric signal generated by the ECM 600R signal generator is characterized by a fast rise time and an exponential tail.

A number of variables are considered in achieving a desired pulse length with the ECM 600R signal generator. These include the type of fluid medium, voltage and timing mode, and volume. In the ECM 600R signal generator, the electroporation pulse length is set by selecting one of ten timing resistors marked R1 through R10. They are active in both High VM (capacitance fixed at fifty microfarads) and Low VM (with a capacitance range from 25 to 3,175 microfarads.

The passage of an electrical current across the cell membrane results in the creation of transient pores which are critical to the electroportion process. The ECM 600R signal generator provides the voltage (in kV) that travels across the chamber gap (in cm) between the electrodes. This potential difference defines what is called the electric field strength where E equals kV/cm. Each cell species has its own critical field strength for optimum electroportion. This is due to cell size, membrane make-up and individual characteristics of the cell wall itself. For example, some Gram positive bacteria are quite resistant to electroporation and require very high field strengths, i.e., greater than 17 kV (cm), before cell death and/or electroporation occurs. Generally, the required field strength varies inversely to the size of the cell.

The ECM 600R signal generator has a knob that permits the adjustment of the amplitude of the set charging voltage applied to the internal capacitors from 50 to 500 volts in low VM and from 0.05 to 2.5 kV in the High VM. The amplitude of the electrical signal is shown on a display incorporated into the ECM 600R signal generator. This device further includes a plurality of push button switches for controlling pulse length, in the LOW VM mode, by a simultaneous combination of resistors parallel to the output and a bank of seven selectable additive capacitors.

The ECM 600R signal generator also includes a single automatic charge and pulse push button. This button may be depressed to initiate both charging of the internal capacitors to set the voltage and to deliver a pulse to the flow-through chamber in an automatic cycle that takes less than five seconds. The manual button may be sequentially pressed to repeatedly apply the predetermined electric field to the tissues adjacent the needles. Alternatively, a repetitive charge/pulse mode may be selected with an adjustable repetition rate.

The waveforms of the electrical signal provided by the signal generator 16 can be an exponentially decaying pulse, a square pulse, a uni-polar oscillating pulse train or a bipolar oscillating pulse train. The electric field strength can be 0.2 kV cm to 20 k V/cm. The pulse length can be ten microseconds to one hundred milliseconds. By way of example, there can be one to one hundred consecutive pulses. Of course the waveform, electric field strength and pulse duration are dependent upon the type of cells and the type of macromolecules that are to enter the cells via electroporation.

FIG. 2 illustrates a second embodiment of the injection and electroporation apparatus of the present invention. Parts similar to those of the first embodiment are labeled with the same reference numeral primed. In the second embodiment the parallel needles 12 are replaced with a pointed blade or spade 24. As shown in the enlarged fragmentary view of FIG. 3, the spade 24 comprises a pair of planar conductive electrodes 26 and 28 which are supported on opposite sides of a planar dielectric support 30 having a pair of elongate channels 32 and 34 formed in the sides thereof. These channels communicate at their rearward ends with the barrel 20 of the syringe 10'. The fluid medium from the barrel 20 is forced through the channels 32 and 34 and out into the adjacent tissues via orifices 36 formed in the edges of the spade 24. The planar electrodes 26 and 28 are connected to the signal generator 16 via cable 18. The advantage of the spade configuration is that a more homogeneous field is produced at the surface of the electrodes. However, this configuration is more suited for a surgical procedure because of the local incision caused by its insertion.

While I have described two preferred embodiments of my injection and electroporation apparatus for drug and gene delivery, it should be understood that modifications and adaptations thereof will occur to persons skilled in the art without departing from the spirit of my invention. Therefore, the protection afforded my invention should only be limited in accordance with the scope of the following claims.

I claim:

1. An apparatus for implanting macromolecules into selected tissues of a patient, comprising:
    means for injecting a predetermined quantity of a fluid medium carrying preselected macromolecules into a preselected tissue region of a patient;
    means for generating a predetermined electric signal; and
    implantable means including a pair of spaced tissue penetrating electrodes for insertion into the tissue region connected to the signal generating means for applying an electric field of a predetermined strength and duration in the tissue region between the electrodes in order to make the walls of a plurality of cells in the tissue region transiently permeable to permit the macromolecules to enter said preselected cells without damaging said cells.

2. An apparatus according to claim 1 the means for injecting the quantity of fluid carrying the macromolecules and the implantable means comprise a syringe.

3. An apparatus for implanting macromolecules into selected tissues of a patient, comprising:
    means including a syringe for injecting a predetermined quantity of a fluid medium carrying preselected macromolecules into a preselected tissue region of a patient;
    means for generating a predetermined electric signal; and
    implantable means including a pair of electrodes connected to the signal generating means for applying an electric field of a predetermined strength and duration in the tissue region in order to make the walls of a plurality of cells in the tissue region transiently permeable to permit the macromolecules to enter said preselected cells without damaging said cells wherein the syringe has a pair of parallel needles that form the electrodes.

4. A method according to claim 3 wherein the electric signal generating means is capable of generating a wave form selected form the group consisting of an exponentially decaying pulse, a square pulse, a uni-polar oscillating pulse train and a bipolar oscillating pulse train.

5. A method according to claim 4 wherein the electric signal generating means is capable of generating a field that has a strength of between approximately 0.2 kV/cm and 20.0 kV/cm.

6. A method according to claim 5 wherein the electric signal generating means is capable of generating each pulse to have a duration of between approximately ten microseconds and one-hundred milliseconds.

7. An apparatus for implanting macromolecules into selected tissues of a patient, comprising:
    means including a syringe for injecting a predetermined quantity of a fluid medium carrying preselected macromolecules into a preselected tissue region of a patient;
    means for generating a predetermined electric signal; and
    implantable means including a pair of electrodes connected to the signal generating means for applying an electric field of a predetermined strength and duration in the tissue region in order to make the walls of a plurality of cells in the tissue region transiently permeable to permit the macromolecules to enter said preselected cells without damaging said cells wherein the syringe has a blade having a dielectric planar support with at least one channel for conveying the fluid and the electrodes are planar and are carried on opposite sides of the support.

8. An apparatus according to claim 7 wherein the planar support has a plurality of orifices along opposite side edges thereof.

9. A method according to claim 7 wherein the electric signal generating means is capable of generating a wave form selected from the group consisting of an exponentially decaying pulse, a square pulse, a uni-polar oscillating pulse train and a bipolar oscillating pulse train.

10. A method according to claim 9 wherein the electric signal generating means is capable of generating a field that has a strength of between approximately 0.2 kV/cm and 20.0 kV/cm.

11. A method of implanting macromolecules into living cells of a patient, comprising the steps of:
   inserting a pair of electrodes in spaced relation into tissue on opposite sides of a preselected tissue region of a patient;
   injecting a predetermined quantity of a fluid medium carrying preselected macromolecules into the tissue region; and
   applying a predetermined electric signal of a predetermined amplitude and duration to the electrodes to generate an electric field of sufficient strength and duration adjacent the electrodes to cause the walls of a plurality of cells in the tissue region to become transiently permeable to permit the macromolecules to enter said preselected cells without damaging said cells.

12. A method according to claim 11 wherein the macromolecules are selected from the group consisting of genes, DNA and pharmaceutical compounds.

13. A method according to claim 12 wherein the electric signal has a wave form selected from the group consisting of an exponentially decaying pulse, a square pulse, a uni-polar oscillating pulse train and a bipolar oscillating pulse train.

14. A method according to claim 13 wherein the electric field has a strength of between approximately 0.2 kV/cm and 20.0 kV/cm.

15. A method according to claim 14 wherein each pulse has a duration of between approximately ten microseconds and one-hundred milliseconds.

16. A method according to claim 15 wherein there are between approximately one pulse and one-hundred consecutive pulses.

17. A method according to claim 11 wherein the electric signal has a wave form selected from the group consisting of an exponentially decaying pulse, a square pulse, a uni-polar oscillating pulse train and a bipolar oscillating pulse train.

18. A method according to claim 11 wherein the electric field has a strength of between approximately 0.2 kV/cm and 20.0 kV/cm.

19. A method according to claim 11 wherein each pulse has a duration of between approximately ten microseconds and one hundred milliseconds.

20. A method according to claim 11 wherein there are between approximately one pulse and one hundred consecutive pulses.

* * * * *